US011389319B2

(12) United States Patent
Botten et al.

(10) Patent No.: US 11,389,319 B2
(45) Date of Patent: Jul. 19, 2022

(54) OSTOMY BARRIER

(71) Applicant: Hollister Incorporated, Libertyville, IL (US)

(72) Inventors: Ronald S. Botten, Gurnee, IL (US); Christina Augustyn, Chicago, IL (US); Russell J. Todd, Evanston, IL (US); Peter L. Visconti, Gurnee, IL (US); Heather M. Budorick, Libertyville, IL (US); Lynn Sacramento, Libertyville, IL (US)

(73) Assignee: Hollister Incorporated, Libertyville, IL (US)

( * ) Notice: Subject to any disclaimer, the term of this patent is extended or adjusted under 35 U.S.C. 154(b) by 529 days.

(21) Appl. No.: 16/339,435

(22) PCT Filed: Nov. 15, 2017

(86) PCT No.: PCT/US2017/061788
§ 371 (c)(1),
(2) Date: Apr. 5, 2019

(87) PCT Pub. No.: WO2018/093891
PCT Pub. Date: May 24, 2018

(65) Prior Publication Data
US 2020/0038226 A1    Feb. 6, 2020

Related U.S. Application Data

(60) Provisional application No. 62/424,723, filed on Nov. 21, 2016.

(51) Int. Cl.
*A61F 5/443* (2006.01)
*A61F 5/44* (2006.01)

(52) U.S. Cl.
CPC ............ *A61F 5/443* (2013.01); *A61F 5/4404* (2013.01)

(58) Field of Classification Search
CPC ........ A61F 5/443; A61F 5/445; A61F 5/4404; A61F 5/451
See application file for complete search history.

(56) References Cited

U.S. PATENT DOCUMENTS

| 5,330,455 A | 7/1994 | McKay |
| 5,811,116 A * | 9/1998 | Gilman ................... A61F 5/443 424/443 |
| 2006/0195053 A1 * | 8/2006 | Oelund ................... A61F 5/443 602/42 |

(Continued)

FOREIGN PATENT DOCUMENTS

| WO | 9415562 A1 | 7/1994 |
| WO | 2013009848 A2 | 1/2013 |

OTHER PUBLICATIONS

International Preliminary Report on Patentability issued by International Bureau in connection with PCT/US2017/061788 dated May 21, 2019.

*Primary Examiner* — Tatyana Zalu Kaeva
*Assistant Examiner* — Hans Kaliher
(74) *Attorney, Agent, or Firm* — Levenfeld Pearlstein, LLC

(57) ABSTRACT

An ostomy barrier includes an inlet opening for receiving a stoma and a barrier adhesive including a plurality of thicker portions and a plurality of thinner portions. The plurality of thinner portions are configured and arranged to improve the flexibility of the ostomy barrier.

8 Claims, 5 Drawing Sheets

(56) References Cited

U.S. PATENT DOCUMENTS

| | | | |
|---|---|---|---|
| 2009/0312685 A1* | 12/2009 | Olsen | A61F 13/0269 |
| | | | 602/54 |
| 2010/0324511 A1* | 12/2010 | Dove | A61F 5/445 |
| | | | 604/338 |
| 2014/0114265 A1* | 4/2014 | Israelson | A61F 5/443 |
| | | | 604/342 |
| 2014/0323941 A1* | 10/2014 | Lee | C09J 7/22 |
| | | | 428/137 |
| 2017/0143535 A1* | 5/2017 | Praame | A61F 5/443 |
| 2018/0235801 A1* | 8/2018 | Oellgaard | A61F 5/443 |

* cited by examiner

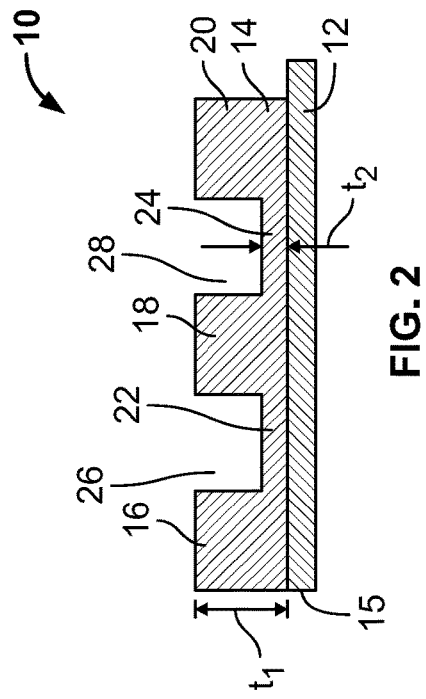
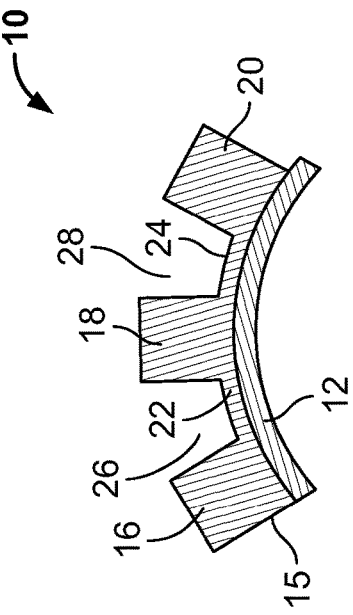
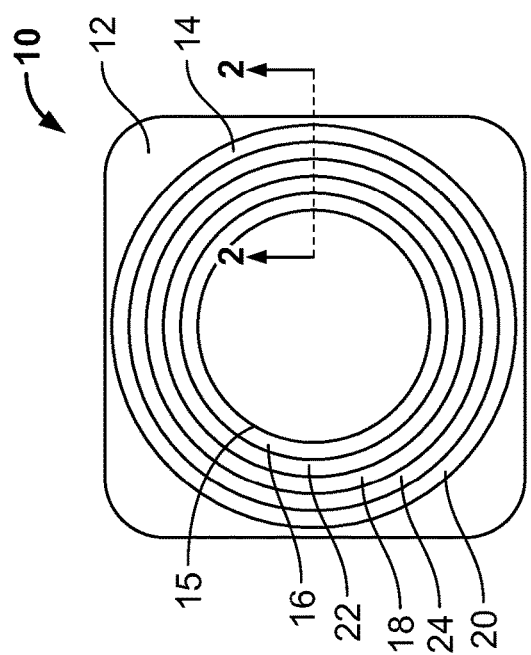
FIG. 1
FIG. 2
FIG. 3
FIG. 4

OSTOMY BARRIER

This is a National Stage Application of International Patent Application No. PCT/US2017/061788, filed Nov. 15, 2017, which claims the benefit of and priority to U.S. Provisional Application No. 62/424,723, filed Nov. 21, 2016, the entirety of which are incorporated fully herein by reference.

BACKGROUND

The following description generally relates to ostomy appliances, and in particular, to an ostomy barrier.

Ostomy pouches for collecting bodily waste are used by individuals who have had surgery such as a colostomy, ileostomy, or urostomy. Ostomy barriers may be used to attach an ostomy appliance, such as an ostomy pouch, to a user, and to seal against peristomal skin surfaces and protect the peristomal surfaces from exposure to stomal effluent.

However, the topography of stomas and peristomal surfaces surrounding stomas varies among patients. Thus, it can be challenging to obtain a secure seal around a stoma, and conventional skin barriers may not provide a reliable seal. Flat barriers do not always contour to non-flat surfaces and convex barriers can be uncomfortable and cause pressure sores. Thus, sealing an ostomy barrier against peristomal surfaces and stomas of various topographies and shapes remains as an area for further improvements.

Accordingly, it is desirable to provide an ostomy barrier configured for improved seal around various stomas and peristomal surfaces.

BRIEF SUMMARY

An ostomy barrier configured for improved flexibility is provided according to various embodiments.

In one aspect, an ostomy barrier for attaching an ostomy appliance to peristomal skin surrounding a stoma is provided. The ostomy barrier may include an inlet opening for receiving a stoma, and a barrier adhesive including a thicker portion and a thinner portion configured to improve flexibility of the ostomy barrier. A thickness the thicker portion may be at least two times a thickness of the thinner portion.

In an embodiment, the thicker portion may include a plurality of thicker concentric barrier rings, and the thinner portion may include a plurality of thinner concentric barrier rings. The plurality of thicker concentric barrier rings and the plurality of thinner concentric rings may be arranged about the inlet opening sharing a common center point. For example, the plurality of thicker concentric barrier rings may include a first thicker barrier ring, a second thicker barrier ring, and a third thicker barrier ring, and the plurality of thinner concentric barrier rings may include a first thinner barrier ring and a second thinner barrier ring. The first thicker barrier ring and the second thicker barrier ring may be separated by the first thinner barrier ring. The second thicker barrier ring and the third thicker barrier ring may be separated by the second thinner barrier ring.

In another embodiment, the thinner portion may include a plurality of indented lines extending on the barrier adhesive. The plurality of indented lines may be configured to function as living hinges to allow the ostomy barrier to crease and bend with a user. The plurality of indented lines may be provided on a distal surface of the barrier adhesive. Alternatively, the plurality of indented lines may be provided on a body-side surface of the barrier surface. In such an embodiment, the inlet opening may be surrounded by a thicker portion, such that the thicker portion surrounding the inlet opening may be attached to the peristomal skin around the user's stoma when the ostomy barrier is attached to the user. The plurality of indented lines may extend horizontally, generally parallel to the user's waist, such that the ostomy barrier may bend along the indented lines according to user's movements. Alternatively, the plurality of indented lines may extend radially from the inlet opening or proximate inlet opening to an outer periphery of the barrier adhesive.

In any of the forgoing embodiments, the thicker portion may have a thickness of about 0.045 inches to about 0.065 inches, while the thinner portion may have a thickness of about 0.010 inches to about 0.015 inches.

The barrier adhesive may be formed from at least one hydrocolloid adhesive. In some embodiments, the thicker portion and the thinner portion may be formed from different materials, in which the thicker portion is formed from a hydrocolloid adhesive.

The ostomy barrier of the any of the foregoing embodiments may be configured for a one-piece ostomy pouch system. In such an embodiment, a backing layer may be disposed on a distal surface of the barrier adhesive, and an ostomy pouch may be attached to the backing layer on the distal surface. Alternatively, the ostomy barrier may be configured for a two-piece ostomy pouch system. In such an embodiment, a backing layer may be disposed on a distal surface of the barrier adhesive, to which a body-side coupling ring may be attached for engaging a pouch-side coupling ring to attach an ostomy pouch to the ostomy barrier.

In another aspect, an ostomy barrier may comprise an inlet opening for receiving a stoma and a barrier adhesive including a plurality of thicker portions defined by a plurality of ring-shaped portions and a plurality of thinner portions defined a plurality of ring-shaped portions. The barrier adhesive may be configured such that adjacent thicker portions are separated by at least one of the plurality of the thinner portions.

In some embodiments, the plurality of thicker portions may comprise a plurality of thicker concentric barrier rings, and the plurality of thinner portions may comprise a plurality of thinner concentric barrier rings. Adjacent thicker concentric barrier rings may be separated by a thinner concentric barrier ring. The plurality of thicker concentric barrier rings and the plurality of thinner concentric barrier rings may be arranged about the inlet opening sharing a common center point.

In yet another aspect, an ostomy barrier may comprise an inlet opening for receiving a stoma and a barrier adhesive including a plurality of thinner portions defined by a plurality of indented lines extending on the barrier adhesive. The plurality of indented lines may be configured to function as living hinges to allow the ostomy barrier to crease and bend with a user when the ostomy barrier is attached to the user.

In an embodiment, the plurality of the indented lines may extend horizontally, generally parallel to a user's, such that the ostomy barrier may bend along the plurality of thinner portions formed by the indented lines with the user. In another embodiment, the plurality of indented lines may extend radially between the inlet opening and a peripheral edge of the barrier adhesive.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein:

FIG. 1 is a schematic top view of an ostomy barrier according to an embodiment;

FIG. 2 is a schematic cross-sectional view of the ostomy barrier of FIG. 1 taken along line A-A;

FIG. 3 is a schematic cross-sectional view of the ostomy barrier of FIG. 1 flexed in one direction;

FIG. 4 is a schematic cross-sectional view of the ostomy barrier of FIG. 1 flexed in another direction;

DETAILED DESCRIPTION

Figure 5:
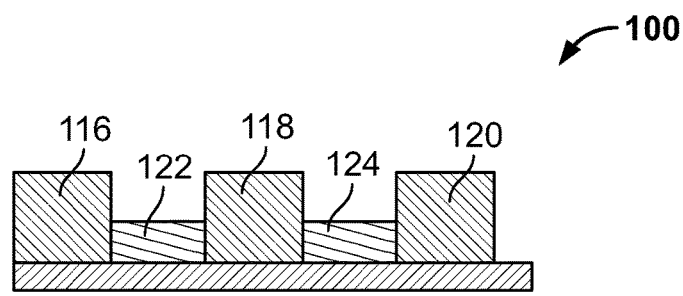
FIG. 5 is a schematic cross-sectional view of an ostomy barrier according to another embodiment.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring to FIGS. 1-4, an ostomy barrier 10 according to an embodiment is shown. The ostomy barrier 10 may generally include a barrier adhesive 14 comprising at least two thicker portions 16, 18, 20 (three such thicker portions being shown) and at least one thinner portion 22, 24 (two such thinner portions being shown) disposed on a backing layer 12, and an inlet opening 15 for receiving a stoma. The at least two thicker portions 16, 18, 20 are separated from each other by at least one thinner portion 22, 24 therebetween. In an embodiment, a thickness of each of the thicker portions 16, 18, 20 may be at least two times a thickness of each of the at least one thinner portions 22, 24. As such, a spacing 26, 28 is defined by a gap between the thicker portions 16, 18, 20, which may allow the ostomy barrier 10 to bend and flex more freely to better conform to a user's body when compared to conventional ostomy barriers including a barrier having generally one constant thickness.

In the embodiment of FIGS. 1-4, the at least two thicker portions 16, 18, 20 comprise three concentric barrier rings including an inner barrier ring 16, a middle barrier ring 18, and an outer barrier ring 20, in which the barrier rings 16, 18, 20 share a common center point with the inlet opening 15. The inner barrier ring 16 has a smallest diameter and the diameter of the barrier rings increases from the inner barrier ring 16 to the outer barrier ring 20. The thinner portions 22, 24 comprise two concentric barrier rings including a first thinner barrier ring 22 and a second thinner barrier ring 24. The inner barrier ring 16 is separated from the middle barrier ring 18 by the first thinner barrier ring 22 arranged therebetween. The middle barrier ring 18 is separated from the outer barrier ring 20 by the second thinner barrier ring 24 arranged therebetween.

Each of the thicker portions 16, 18, 20 may have the same thickness or different thicknesses. The thickness of the each of the thicker portions 16, 18, 20 may be about 0.025 inches to about 0.085 inches, preferably about 0.035 inches to about 0.075 inches, more preferably about 0.045 inches to about 0.065 inches. In the embodiment of FIGS. 1-4, each of the thicker portions 16, 18, 20 has the same thickness $t_1$ of about 0.045 inches to about 0.065. The thickness $t_1$ of the thicker portions 16, 18, 20 may be at least two times a thickness of $t_2$ of the thinner portions 22, 24, preferably three times, and more preferably four times. In other embodiments, each of the thicker portions 16, 18, 20 may have a different thickness. For example, a thickness of the inner barrier ring 16 may be thicker than the middle and outer barrier rings 18, 20.

Each of the thinner portions 22, 24 may have the same thickness or different thicknesses. The thickness of the each of the thinner portions 22, 24 may be about 0.002 inches to about 0.035 inches, preferably about 0.005 inches to about 0.025 inches, more preferably about 0.010 inches to about 0.015 inches. In the embodiment of FIGS. 1 and 2, each of the thinner portions 22, 24 has the same thickness $t_2$ of about 0.010 inches to about 0.015 inches.

A spacing may be defined by a gap between adjacent thicker portions due to a thickness difference between the thicker portions and the thickness of a thinner portion arranged therebetween. In the embodiment of FIGS. 1-4, a first spacing 26 is defined between the inner and middle barrier rings 16, 18, and a second spacing 28 is defined between the middle and outer barrier rings 18, 20. The reduced barrier adhesive thickness in the thinner portions 22, 24 and the spacings 26, 28 between the thicker portions 16, 18, 20 allow the ostomy barrier 10 to be more flexible than conventional ostomy barriers having one constant adhesive thickness comparable to the thicker portions 16, 18, 20. As shown in FIGS. 3 and 4, the thinner portions 22, 24 may bend, flex, and stretch more easily compared to the thicker portions 16, 18, 20 to allow the ostomy barrier 10 to better conform to the body contour of a user.

The barrier adhesive 14 may be formed from at least one suitable adhesive, such as a hydrocolloid adhesive or an acrylic adhesive. The thicker portions 16, 18, 20 and the thinner portions 22, 24 may be formed from the same adhesive or different adhesives. In the embodiment of FIGS. 1-4, the inner, middle, and outer barrier rings 16, 18, 20, and the first and second thinner barrier rings 22, 24 may be formed from the same hydrocolloid adhesive.

In some embodiments, the at least two thicker portions may comprise two concentric barrier rings or more than three concentric barrier rings, and the at least one thinner portion may comprise one concentric barrier ring or more than two concentric barrier rings. In other embodiments, the thicker portions and thinner portions may comprise barrier rings of various shapes. For example, the thicker and thinner portions may comprise a plurality of oval-shaped rings, rectangular-shaped rings, triangular-shaped rings, etc. Further, the barrier rings may not be concentrically arranged and may not share a common center point.

FIG. 5 is a schematic cross sectional view of an ostomy pouch 100 according to another embodiment. In this embodiment, the thicker portions 116, 118, 120 may be formed from a hydrocolloid adhesive, while the thinner portions 122, 124 are formed from a different material, which may be a different hydrocolloid adhesive, a different type of adhesive, or a suitable flexible non-adhesive material. For example, the thinner portions 122, 124 may be formed from an adhesive having higher flexibility than the hydrocolloid adhesive of the thicker portions 116, 118, 120. In another example, the thicker portions 116, 118, 120 may be formed from an adhesive having a higher water absorption rate than the material of the thinner portions 122, 124.

Figure 11:
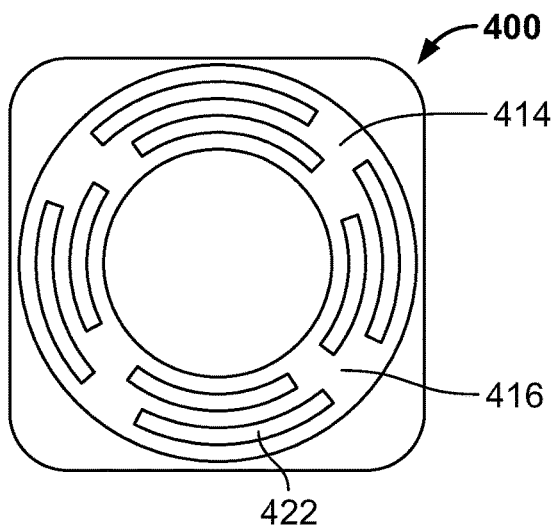
FIG. 11 is a schematic top view of an ostomy barrier according to an embodiment.

In some embodiments, the thinner portions may be provided in a discontinuous pattern. For example, an ostomy barrier 400 of FIG. 11 may include a barrier adhesive 414 including a thicker portion 416 and a plurality of thinner portions 422 arranged therein. The plurality of thinner portions 422 may be configured and arranged to improve flexibility of the ostomy barrier 400 when attached to a user. In this embodiment, the plurality of thinner portions 422 includes eight thinner portions, wherein each of the thinner portions 422 is surrounded by the thicker portion 416. In other embodiments, there may be less than eight thinner portions or more than eight thinner portions, which are configured and arranged among at least one thicker portion to improve flexibility of an ostomy barrier when attached to a user to allow the ostomy barrier to bend and move with the user's body.

Figure 6:
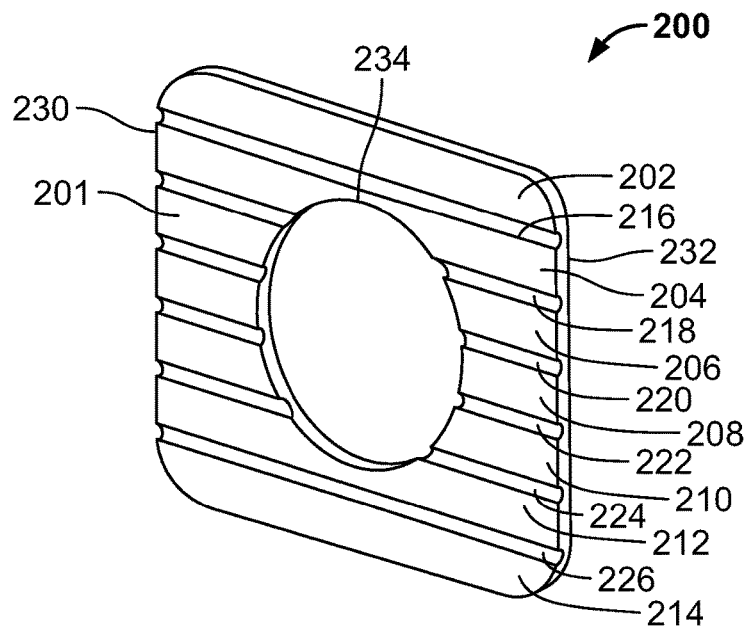
FIG. 6 is a schematic perspective view of an ostomy barrier according to yet another embodiment.
Figure 7:
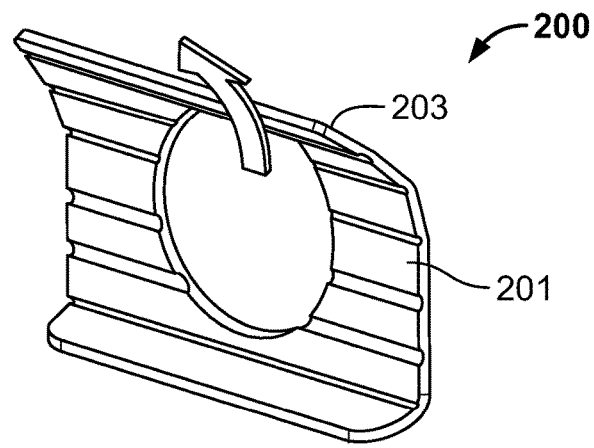
FIG. 7 is a schematic perspective view of the ostomy barrier of FIG. 6 flexed.

FIGS. 6 and 7 illustrate an ostomy barrier 200 according to yet another embodiment. The ostomy barrier 200 may include a barrier adhesive having a distal surface 201 comprising thicker portions 202, 204, 206, 208, 210, 212, 214, and thinner portions 216, 218, 220, 222, 224, 226, and a generally flat body-side surface 203. As shown in FIG. 6, the ostomy barrier 200 may be configured such that adjacent thicker portions are separated by a thinner portion arranged therebetween. In this embodiment, the thinner portions 216, 218, 220, 222, 224, 226 may be defined by indented lines extending horizontally from a peripheral edge 230 to an opposite peripheral edge 232 or from the peripheral edge 230 to an inlet opening 234 or from the inlet opening 234 to the opposite peripheral edge 234. The ostomy barrier 200 may be attached to a user, such that the generally flat body-side surface 203 faces the user and the thinner portions 216, 218, 220, 222, 224, 226 extend generally parallel to the user's waist. When attached to the user, the thinner portions 216, 218, 220, 222, 224, 226 may function as living hinges to allow the ostomy barrier 200 to crease and bend easily with the shape and movement of the user's body as shown in FIG. 7.

Figure 12:
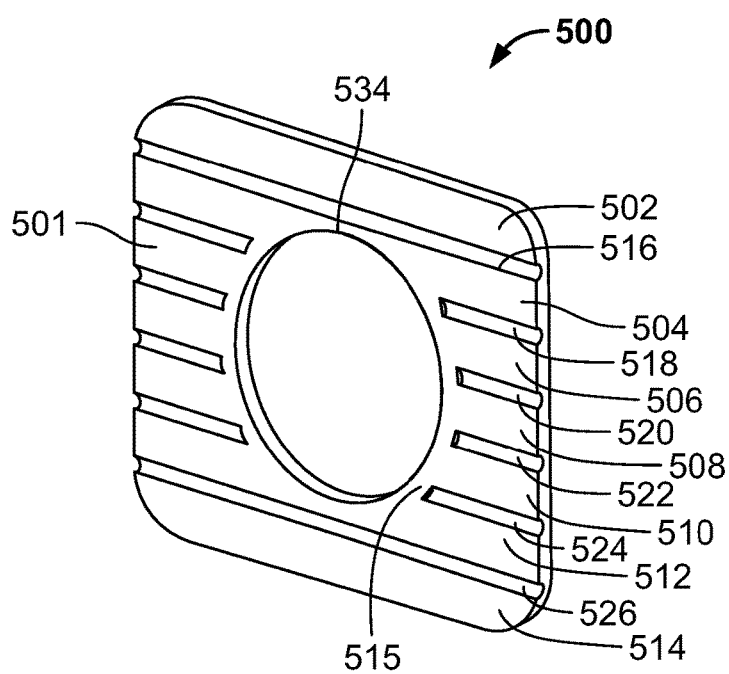
FIGS. 12-15 are schematic perspective views of ostomy barriers according various embodiments.

An ostomy barrier 500 of FIG. 12 may be similarly configured to the ostomy barrier 200 of FIG. 6, except thicker portions 502, 504, 506, 508, 510, 512, 514, and thinner portions 516, 518, 520, 522, 524, 526 are provided on a body-side surface 501. In this embodiment, an inlet opening 534 may be surrounded by a thicker portion 515, such that the thinner portions 518, 520, 522, 524 do not extend to the inlet opening 534. The ostomy barrier 500 may be attached to a user, such that the user's stoma is received through the inlet opening 534 and the thicker portion 515 is attached to a peristomal area surrounding the stoma to prevent body waste from channeling through the thinner portions 518, 520, 522, 524.

Figure 8:
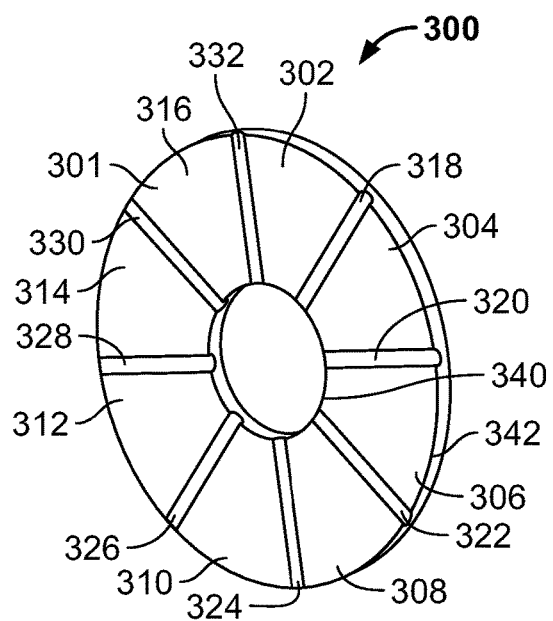
FIG. 8 is a schematic perspective view of an ostomy barrier according to an embodiment.

FIG. 8 illustrates an ostomy barrier 300 according to still another embodiment. The ostomy barrier 300 may include a barrier adhesive having a distal side 301 comprising thicker portions 302, 304, 306, 308, 310, 312, 314, 316 and thinner portions 318, 320, 322, 324, 326, 328, 330, 332, and a generally flat body-side surface. In this embodiment, adjacent thicker portions are separated by a thinner portion arranged therebetween. The thinner portions 318, 320, 322, 324, 326, 328, 330, 332 may be defined by indented lines extending radially from an inlet opening 340 to an outer periphery 342 to improve flexibility to the ostomy barrier 300.

Figure 13:
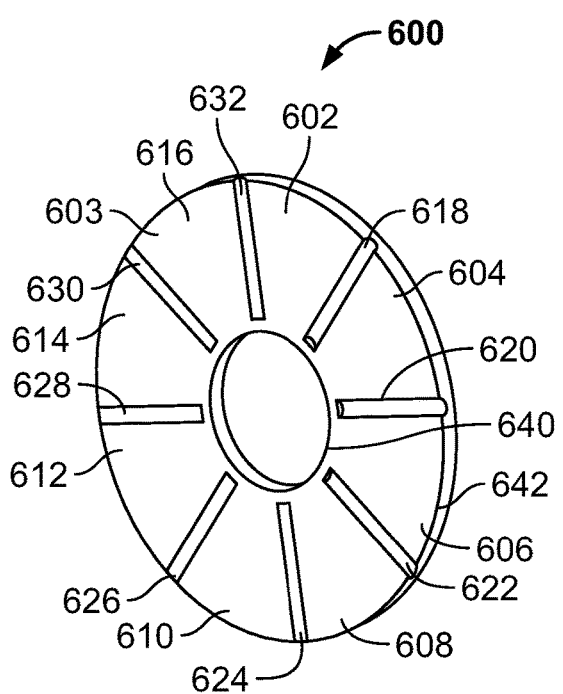
Figure 14:
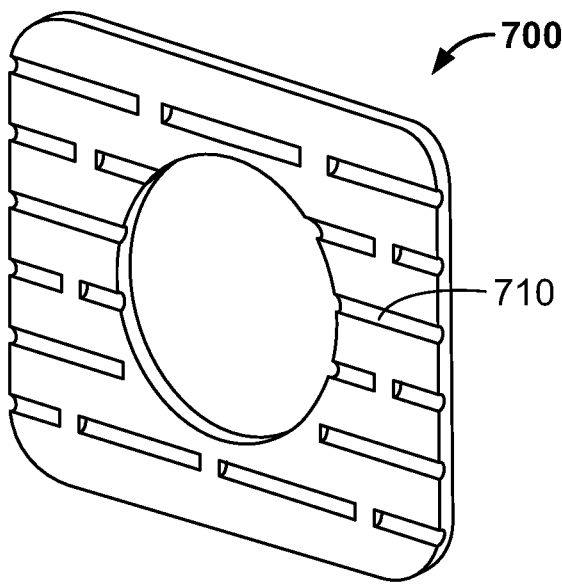
Figure 15:
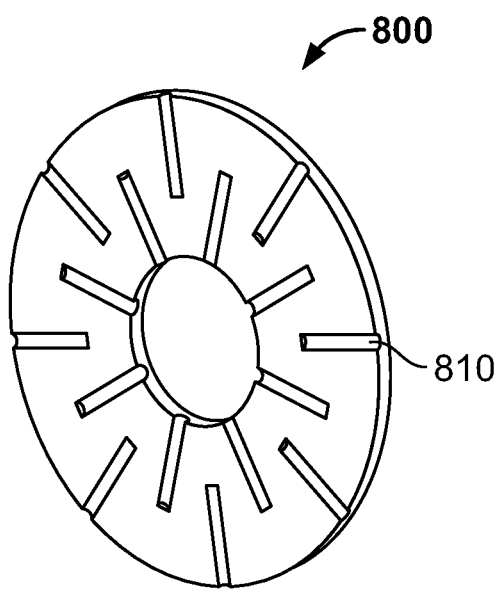

An ostomy barrier 600 of FIG. 13 may be similarly configured to the ostomy barrier 300, except thicker portions 602, 604, 606, 608, 610, 612, 614, 616 and thinner portions 618, 620, 622, 624, 626, 628, 630, 632 are provided on a body-side surface 603. In this embodiment, the thinner portions 618, 620, 622, 624, 626, 628, 630, 632 do not extend to an inlet opening 640, such that the inlet opening 640 is surrounded by a thicker portion similar to the ostomy barrier 500 of FIG. 12. In some embodiments, an ostomy barrier 700, 800 may be configured similar to the ostomy barrier 200, 300, 500, or 600, except thinner portions 710, 810 may be provided in a discontinuous pattern configured to improve flexibility of the ostomy barrier 700, 800 as shown in FIGS. 14, 15. As shown, some of the thinner portions 710, 810 extend to an inlet opening in these embodiments. Thus, in theses embodiments, the surface comprising the thinner portions 710, 810 may define the distal surface of the ostomy barrier 700, 800. In other embodiments, discontinuous thinner portions may be provided on a body-side of an ostomy barrier. In such an embodiment, the discontinuous thinner portions do not extend to an inlet opening of the ostomy barrier.

In some embodiments, an ostomy barrier may be injection molded using one or more barrier adhesives to form the thicker portions and thinner portions as defined in the foregoing embodiments. In other embodiments, an embossing process may be used to form indented lines on a barrier adhesive to define thinner portions.

Figure 9:
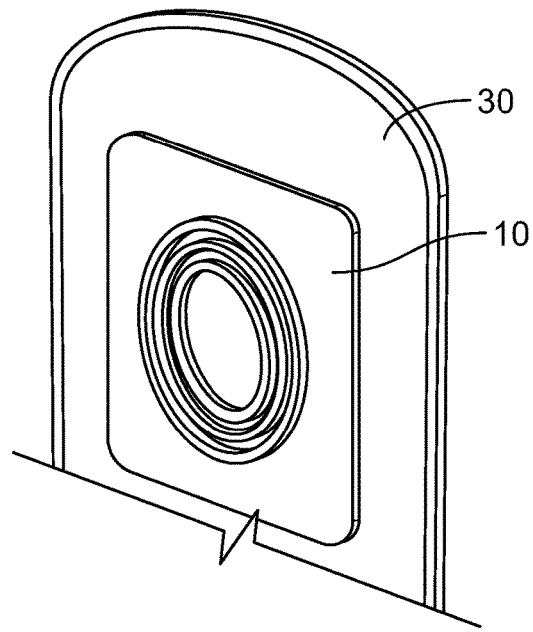
FIG. 9 is a schematic illustration of a one-piece ostomy pouch including the ostomy barrier of FIG. 1 according to an embodiment.
Figure 10:
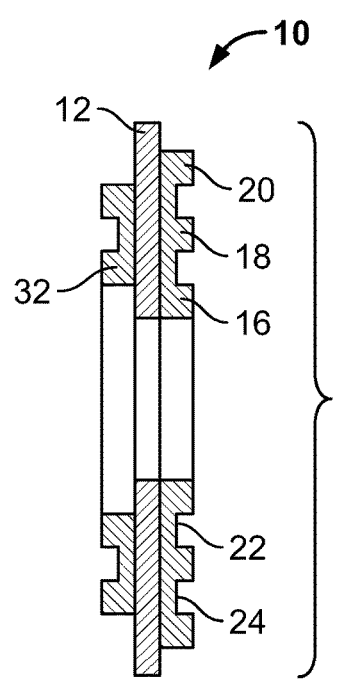
FIG. 10 is a schematic illustration of the ostomy barrier of FIG. 1 including a body-side coupling ring according to an embodiment.

The ostomy barriers of any of the foregoing embodiments may be used to attach an ostomy pouch, such as an ostomy pouch, to a user. For example, an ostomy pouch 30 may be attached to a distal surface of the ostomy barrier 10 as shown in FIG. 9. In another embodiment, the ostomy barrier 10 may include a body-side coupling ring 32 attached to the distal surface and configured to mate with a pouch-side coupling ring (not shown) to attach an ostomy pouch as shown in FIG. 10.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An ostomy barrier for attaching an ostomy appliance to a peristomal skin surrounding a stoma, the ostomy barrier comprising:

an inlet opening for receiving a stoma; and a barrier adhesive including a thicker portion and a thinner portion configured to improve flexibility of the ostomy barrier, wherein a thickness of the thicker portions is at least two times a thickness of the thinner portion, wherein the thinner portions comprise a plurality of indented lines extending horizontally from a peripheral edge to an opposite peripheral edge, wherein the plurality of indented lines extend generally parallel to user's waist, and wherein the plurality of indented lines are configured to function as living hinges to allow the ostomy barrier to crease and bend with a user when the ostomy barrier is attached to the user.

2. The ostomy barrier of claim 1, wherein the barrier adhesive has a distal surface and a body-side surface, wherein the plurality of indented lines are provided on the distal surface, and wherein the ostomy barrier is configured to attached to a user by adhering the body-side surface to the user.

3. The ostomy barrier of claim 1, wherein the barrier adhesive has a distal surface and a body-side surface, wherein the plurality of indented lines are provided on the body-side surface, wherein the inlet opening is surrounded by the thicker portion, and wherein the ostomy barrier is configured to attach to a user by adhering the body-side surface to the user.

4. The ostomy barrier of claim 1, wherein the thicker portion has a thickness of about 0.045 inches to about 0.065 inches, and the thinner portion has a thickness of about 0.010 inches to about 0.015 inches.

5. The ostomy barrier of claim 1, wherein the barrier adhesive is formed from at least one hydrocolloid adhesive.

6. The ostomy barrier of claim 1, wherein the thicker portion is formed from a first material and the thinner portion is formed from second material that is different from the first material, wherein the first material is a hydrocolloid adhesive.

7. The ostomy barrier of claim 1, wherein a backing layer is disposed on a distal surface of the barrier adhesive, and an ostomy pouch is attached to the backing layer on the distal surface of the barrier adhesive.

8. The ostomy barrier of claim 1, wherein a backing layer is disposed on a distal surface of the barrier adhesive, and a body-side coupling ring is attached to the backing layer on the distal surface of the barrier adhesive, wherein the body-side coupling ring is configured to mate with a pouch-side coupling ring attached to an ostomy pouch for attaching the ostomy pouch to the ostomy barrier.

\* \* \* \* \*